US012810994B2

(12) United States Patent
Nagao

(10) Patent No.: US 12,810,994 B2
(45) Date of Patent: Nov. 24, 2026

(54) MEDICAL IMAGE DISPLAY APPARATUS, RECORDING MEDIUM, AND MEDICAL IMAGE DISPLAY SYSTEM

(71) Applicant: Konica Minolta, Inc., Tokyo (JP)

(72) Inventor: Kenji Nagao, Tokorozawa (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 18/610,330

(22) Filed: Mar. 20, 2024

(65) Prior Publication Data

US 2024/0331843 A1 Oct. 3, 2024

(30) Foreign Application Priority Data

Mar. 30, 2023 (JP) ................................ 2023-054787

(51) Int. Cl.
*G16H 30/20* (2018.01)
*G16H 10/60* (2018.01)
*G16H 30/40* (2018.01)

(52) U.S. Cl.
CPC ............. *G16H 30/20* (2018.01); *G16H 10/60* (2018.01); *G16H 30/40* (2018.01)

(58) Field of Classification Search
CPC ......... G16H 30/20; G16H 10/60; G16H 30/40
See application file for complete search history.

(56) References Cited

U.S. PATENT DOCUMENTS

2021/0158938 A1* 5/2021 Arlagadda ............. G16H 30/40
2021/0256009 A1* 8/2021 Zhang ................... H04L 9/3239

FOREIGN PATENT DOCUMENTS

JP 2005182179 A 7/2005
JP 2015114695 A * 6/2015

OTHER PUBLICATIONS

JPO Notice of Reasons for Refusal for corresponding JP Application No. 2023-054787; Issued Jun. 16, 2026.

* cited by examiner

*Primary Examiner* — Joshua B Blanchette
(74) *Attorney, Agent, or Firm* — CANTOR COLBURN LLP

(57) ABSTRACT

A medical image display apparatus includes: a display that displays, through a first viewer, a first medical image stored in a first server; and a hardware processor that obtains a related medical image that is a second medical image related to the first medical image and is displayable through a second viewer, from a second server that stores the second medical image, wherein the display displays, through the first viewer, the related medical image obtained by the hardware processor.

11 Claims, 17 Drawing Sheets

FIG. 9

| KANJI NAME | KANA NAME | ALPHABETICAL NAME | BIRTH DATE | GENDER | FACILITY | EXAMINATION DATE | MODALITY | IMAGING PORTION |
|---|---|---|---|---|---|---|---|---|
| Sato Masaru | Sato Masaru | Sato Masaru | 1960/1/1 | MALE | B HOSPITAL | 2022/11/1 | CR | CHEST |
| Sato Masaru | Sato Masaru | Sato Masaru | 1960/1/1 | MALE | B HOSPITAL | 2023/1/16 | CT | HEAD |
| Sato Masaru | Sato Masaru | Sato Masaru | 1960/1/1 | MALE | B HOSPITAL | 2021/10/1 | CR | ABDOMINAL POSITION |
| Sato Masaru | Sato Masaru | Sato Masaru | 1960/1/1 | MALE | B HOSPITAL | 2020/1/10 | CR | TRACHEA |
| Sato Masaru | Sato Masaru | Sato Masaru | 1960/1/1 | MALE | B HOSPITAL | 2021/6/1 | MR | TRACHEA |
| Sato Masaru | Sato Masaru | Sato Masaru | 1960/1/1 | MALE | B HOSPITAL | 2019/9/1 | CR | HEAD |
| | | | | | | | | |

FIG. 15

| FACILITY NAME | RELATED PATIENT NAME | EXAMINATION DATE | OBTAINMENT |
|---|---|---|---|
| FACILITY A | TANAKA ICHIRO | 2023/3/3 | DONE |
| FACILITY B | TANAKA ICHIRO | 2023/1/13 | DONE |
| FACILITY C | TANAKA ICHIRO | 2023/2/14 | — Download |

G

FIG. 17

| FACILITY NAME | COMMON ID | PATIENT ID | RELATED PATIENT NAME | BIRTH DATE | EXAMINATION ID | EXAMINATION DATE | RELATED PATIENT |
|---|---|---|---|---|---|---|---|
| OWN FACILITY | CM0001 | JS0001 | TANAKA ICHIRO | 1975/5/3 | ST001 | 2023/3/3 | PRESENT |
| FACILITY A | CM0001 | TS0001 | TANAKA ICHIRO | 1975/5/3 | ST004 | 2023/1/13 | — |
| FACILITY B | CM0001 | TS0001 | TANAKA ICHIRO | 1975/5/3 | ST005 | 2023/2/14 | H I |

FIG. 18

| FACILITY NAME | COMMON ID | PATIENT ID | RELATED PATIENT NAME | BIRTH DATE | EXAMINATION ID | EXAMINATION DATE | RELATED PATIENT |
|---|---|---|---|---|---|---|---|
| OWN FACILITY | CM0001 | JS0001 | TANAKA ICHIRO | 1975/5/3 | ST001 | 2023/3/3 | PRESENT |
| FACILITY A | CM0001 | TS0001 | TANAKA ICHIRO | 1975/5/3 | ST004 | 2023/1/13 | J K |
| FACILITY B | CM0001 | TS0001 | TANAKA ICHIRO | 1975/5/3 | ST005 | 2023/2/14 | J K |

FIG. 19

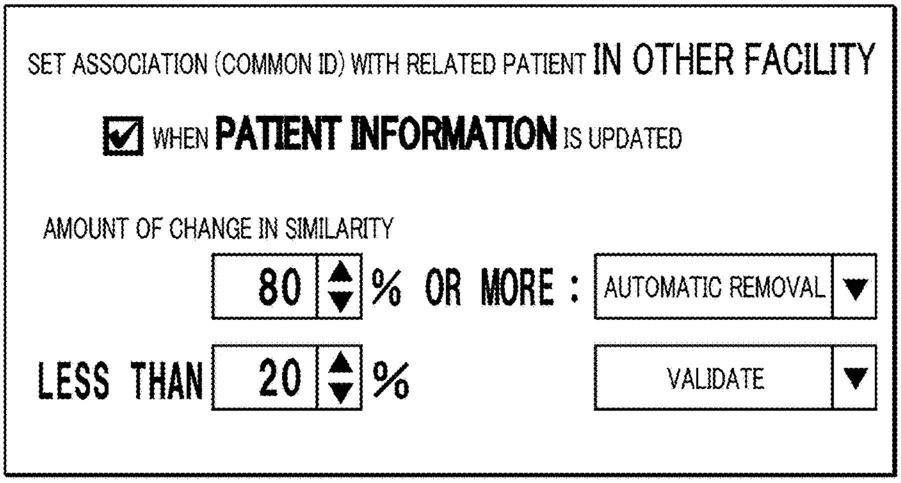

MEDICAL IMAGE DISPLAY APPARATUS, RECORDING MEDIUM, AND MEDICAL IMAGE DISPLAY SYSTEM

CROSS REFERENCE TO PRIOR APPLICATIONS

The present invention claims priority under 35 U.S.C. § 119 to Japanese Application No. 2023-054787 filed Mar. 30, 2023, the entire content of which is incorporated herein by reference.

BACKGROUND OF THE INVENTION

Technical Field

The present invention relates to a medical image display apparatus, a recording medium, and a medical image display system.

Description of Related Art

Conventionally, a medical image display apparatus displays, on a display, a medical image taken in an own medical facility using a local application that is executed in a system in the own medical facility. The application is an application program or application software. The medical image display apparatus displays, on the display, a medical image taken in another medical facility, using a web application for reference via the Internet.

A case is described where the medical image taken in the own medical facility, and the medical image taken in the other medical facility are subjected to comparative interpretation. In this case, a user is required to use two different viewers that are a local application and a web application. Accordingly, the comparative interpretation is difficult.

To address the problem that the comparative interpretation is difficult, JP 2015-114695A discloses the following technique. Specifically, the technique obtains a plurality of medical care images respectively generated by a plurality of applications and displays the obtained medical care images on a single integrated viewer in a combined manner.

The technique disclosed in JP 2015-114695A can juxtapose and display the medical care images generated by the respective applications, on the integrated viewer. Accordingly, the problem of difficulty in comparative interpretation can be solved.

SUMMARY OF THE INVENTION

According to the conventional art, a user interprets the medical images through predetermined operations, on the integrated viewer instead of the individual applications. The predetermined operations include operations for a real-time gradation process, rescaling and the like to be performed during interpretation.

Accordingly, the user performs interpretation on the integrated viewer about which the user is inexperienced in operation, instead of the local application in the own medical facility about which the user is experienced in operation. Consequently, there is a problem that the efficiency of interpretation is low.

There is another problem that the user cannot use operations and functions distinctive to each application during interpretation. The operations and functions distinctive to the corresponding application are functions that require complicated operations, such as displaying and operation on a 3D viewer, adjustment and annotation, and bone mineral quantitative measurement.

The present invention has been made in view of the problems described above and has an object to provide a medical image display apparatus, a recording medium, and a medical image display system that allow preferable interpretation of medical images.

To achieve at least one of the abovementioned objects, according to an aspect of the present invention, a medical image display apparatus reflecting one aspect of the present invention includes:

- a display that displays, through a first viewer, a first medical image stored in a first server; and
- a hardware processor that obtains a related medical image that is a second medical image related to the first medical image and is displayable through a second viewer, from a second server that stores the second medical image,
- wherein
- the display displays, through the first viewer, the related medical image obtained by the hardware processor.

To achieve at least one of the abovementioned objects, according to an aspect of the present invention, a recording medium reflecting one aspect of the present invention is

- a non-transitory computer readable recording medium storing a program causing a computer of a medical image display apparatus to:
- cause a display to display, through a first viewer, a first medical image stored in a first server; and
- obtain a related medical image that is a second medical image related to the first medical image and is displayable through a second viewer, from a second server that stores the second medical image,
- wherein the program causes the computer to display the obtained related medical image through the first viewer.

To achieve at least one of the abovementioned objects, according to an aspect of the present invention, a medical image display system reflecting one aspect of the present invention includes:

- a first server that stores a first medical image displayable through a first viewer;
- a second server that stores a second medical image displayable through a second viewer; and
- a medical image display apparatus that displays a medical image,
- wherein the medical image display apparatus comprises:
- a display that displays, through the first viewer, the first medical image stored in the first server; and
- a hardware processor that obtains a related medical image that is the second medical image related to the first medical image, from the second server, and
- the display displays, through the first viewer, the related medical image obtained by the hardware processor.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 9 shows an example of an examination list of a related patient.

FIG. 15 shows an example of a related patient list in the modified example,

FIG. 17 shows an example of the examination list in the modified example, FIG. 18 shows an example of the examination list in the modified example; and FIG. 19 shows an example of a common ID setting screen in the modified example.

DETAILED DESCRIPTION

Hereinafter, one or more embodiments of the present invention will be described with reference to the drawings. However, the scope of the invention is not limited to the disclosed embodiments.

[Medical Image Display System]

Figure 1:
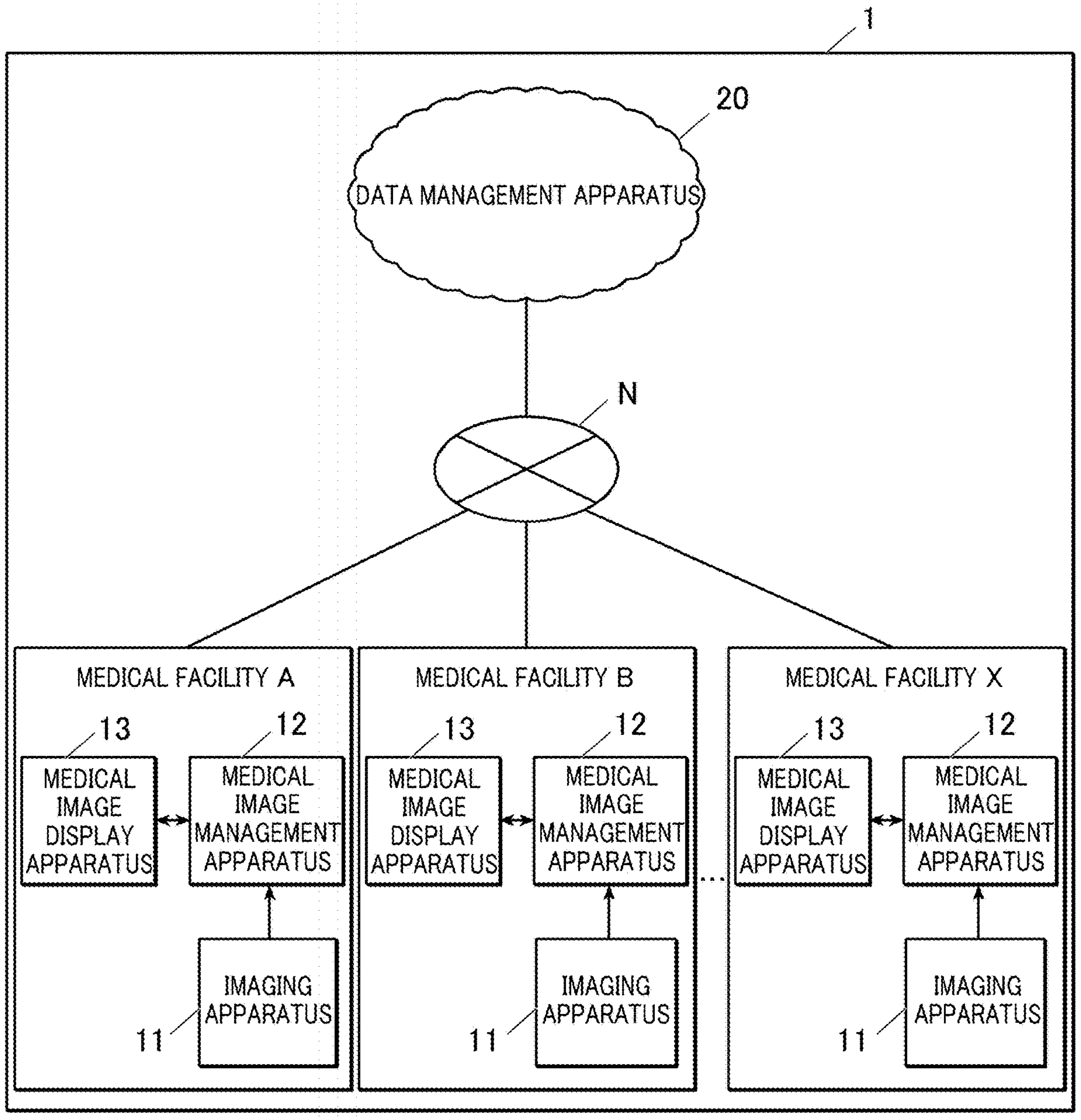
FIG. 1 is a system configuration diagram of a medical image display system according to the present embodiment.

FIG. 1 shows a configuration of a medical image display system 1.

The medical image display system 1 includes imaging apparatuses 11, medical image management apparatuses 12, and medical image display apparatuses 13, in a plurality of medical facilities A, B, . . . , X. Each medical image management apparatus 12 is a first server.

The medical image display system 1 includes a data management apparatus 20. The data management apparatus 20 is a second server.

The apparatuses constituting the medical image display system 1 are connected to each other via a communication network N, such as a local area network (LAN), a wide area network (WAN), and the Internet.

The apparatuses constituting the medical image display system 1 each conform to the Health Level Seven (HL7) or Digital Image and Communications in Medicine (DICOM) standard. Accordingly, communication between the apparatuses is performed in conformity with the HL7 or DICOM.

[Imaging Apparatus]

The imaging apparatus 11 is, for example, an X-ray radiography apparatus (DR or CR), an ultrasonic diagnostic apparatus (US), or an image generation apparatus, such as one for CT or MRI.

The imaging apparatus 11 receives examination order information transmitted from a radiology information system (RIS), not shown, or the like. The imaging apparatus 11 takes an image of an examination target portion of a patient as a subject, based on the examination order information, and generates a medical image as medical information.

In the medical image generated in the imaging apparatus 11, supplementary information (such as patient information, examination information, and an image ID) is written to, for example, the header of an image file in conformity with the DICOM standard. The medical image to which the supplementary information is attached is transmitted to the medical image management apparatus 12 through a console, not shown, or the like. A configuration may be adopted where the console transmits the medical image to an image analysis apparatus from the console, and the console transmits an analysis image having been subjected to a predetermined analysis process, to the medical image management apparatus 12.

[Medical Image Management Apparatus]

The medical image management apparatus 12 is, for example, a server constituting a picture archiving and communication system (PACS).

The medical image management apparatus 12 receives the medical image from the imaging apparatus 11. Next, the medical image management apparatus 12 associates the medical image with patient information, examination information, the image ID of the medical image, a facility ID of a medical facility and the like and stores them in a database. Next, the medical image management apparatus 12 transmits a copy of the stored medical image to the data management apparatus 20.

[Medical Image Display Apparatus]

The medical image display apparatus 13 is an apparatus that displays a medical image taken in a designated examination.

Figure 2:
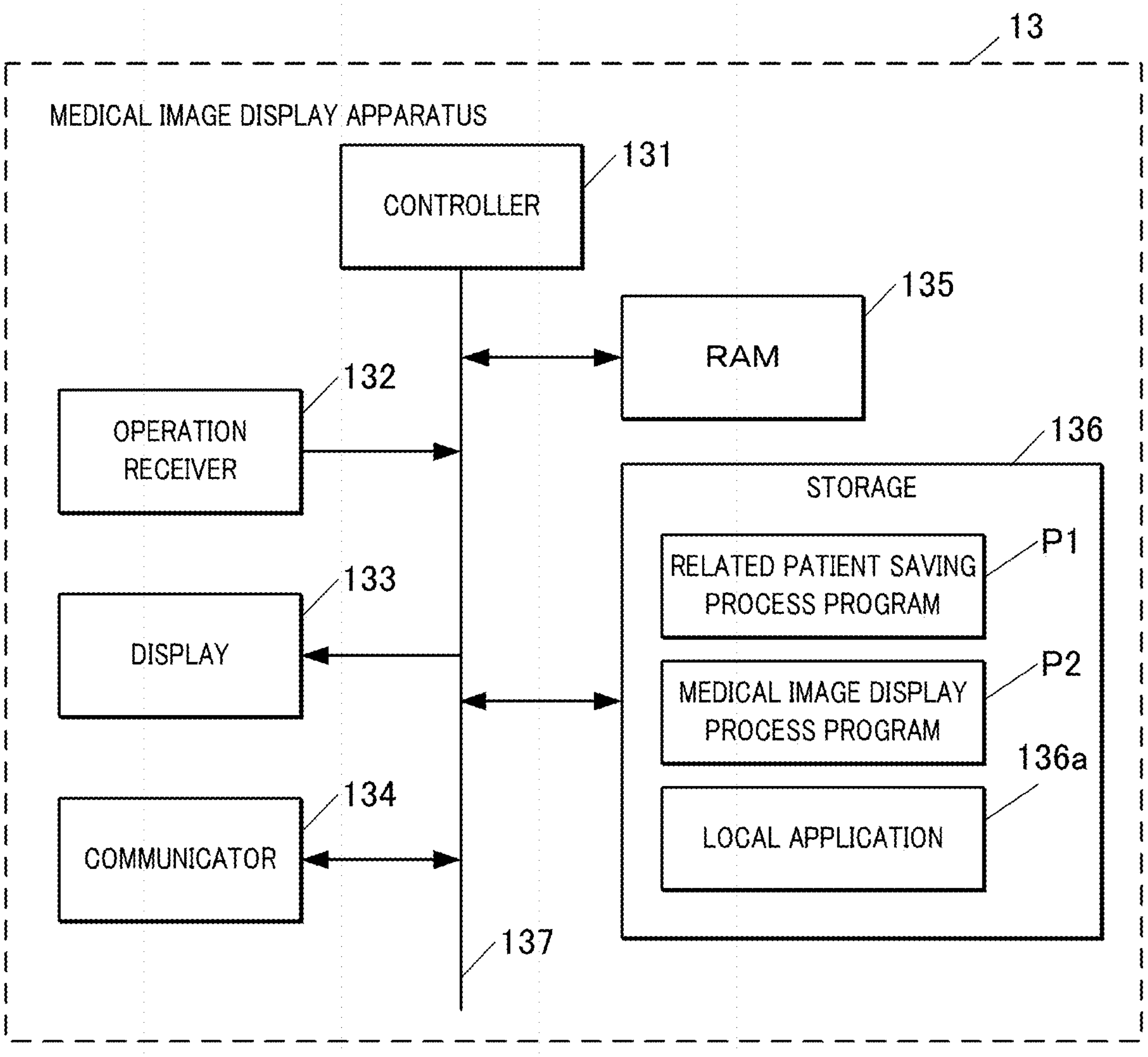
FIG. 2 is a block diagram showing a functional configuration of a medical image display apparatus.

FIG. 2 is a block diagram showing a functional configuration of the medical image display apparatus 13.

The medical image display apparatus 13 includes a controller 131 (hardware processor), an operation receiver 132, a display 133, a communicator 134, a random access memory (RAM) 135, a storage 136, and the like. The individual components of the medical image display apparatus 13 are connected to each other by a bus 137.

The controller 131 includes a central processing unit (CPU), and the like.

The controller 131 reads a system program and various processing programs stored in the storage 136 and loads the programs in a work area formed in the RAM 135. The controller 131 controls the components according to the programs.

The operation receiver 132 includes a keyboard that includes cursor keys, character input keys, and various functional keys, or the like, and a pointing device, such as a mouse.

The operation receiver 132 outputs, to the controller 131, an instruction signal input through a key operation to the keyboard, or a mouse operation.

The operation receiver 132 may have a configuration that includes a touch panel formed so as to cover the display 133.

The display 133 includes a monitor, such as a liquid crystal display (LCD).

The display 133 displays various screens and the like according to an instruction of a display signal input from the controller 131.

The communicator 134 includes an LAN adapter, a router, and a terminal adapter (TA), or the like.

The communicator 134 transmits and receives data to and from an external apparatus connected to the communication network.

The RAM 135 allows the work area to be formed. The work area temporarily stores various programs read from the storage 136, input or output data, parameters and the like, in various processes executed and controlled by the controller 131.

The storage 136 includes a hard disk, and a non-volatile semiconductor memory, or the like.

The storage 136 stores the system program and various processing programs to be executed by the controller 131, and data required for execution of these programs. The storage 136 stores, for example, a web browser program for achieving a web browser, and the like.

The storage 136 stores a related patient saving process program P1, a medical image display process program P2, and the like.

The storage 136 includes a local viewer application program (hereinafter, a local application 136*a*).

The controller 131 causes the display 133 to display the medical image stored in the medical image management apparatus 12, through the local application 136*a*. That is, the local application 136*a* (first viewer) displays a first medical image stored in the medical image management apparatus 12 (first server).

The user who operates the medical image display apparatus 13 refers to the medical image, using the local application 136*a*.

[Data Management Apparatus]

The data management apparatus 20 is, for example, a virtual apparatus provided in a cloud environment.

Figure 3:
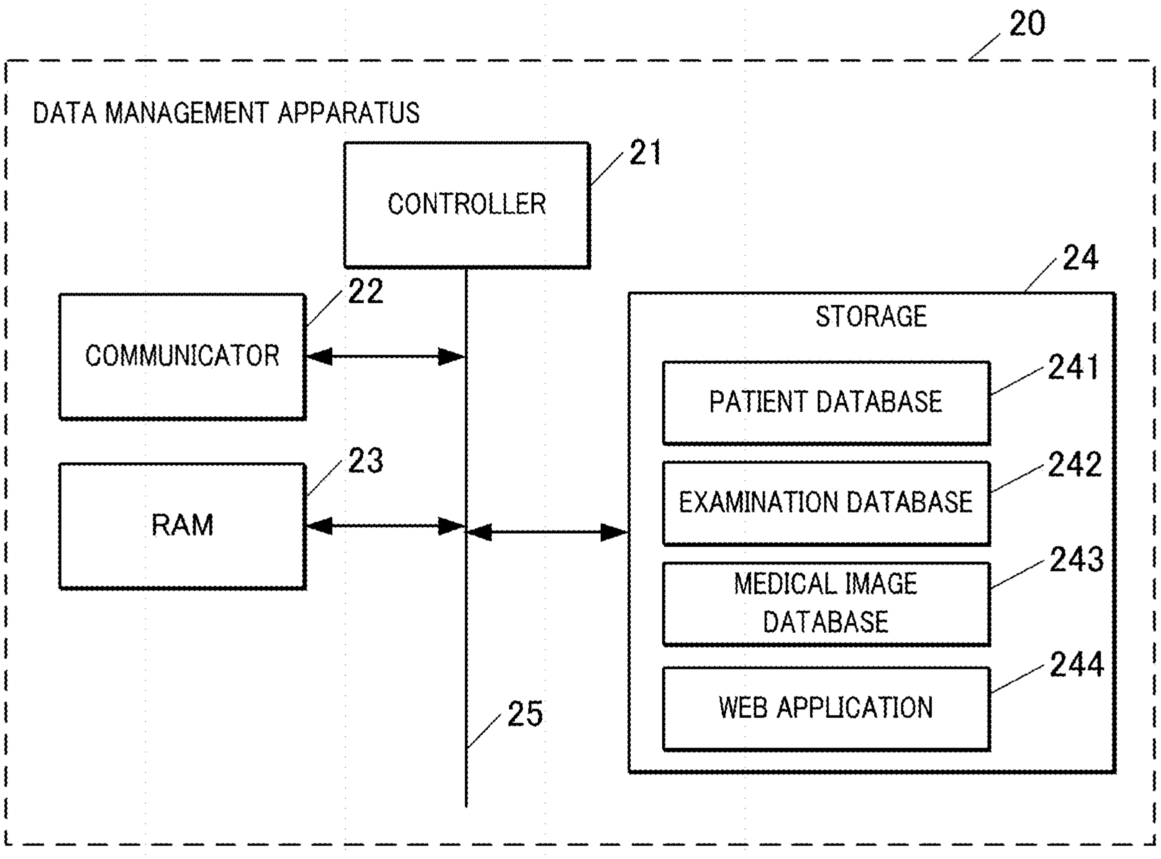
FIG. 3 is a block diagram showing a functional configuration of a data management apparatus.

FIG. 3 is a block diagram showing a functional configuration of the data management apparatus 20.

The data management apparatus 20 includes a controller 21, a communicator 22, a RAM 23, and a storage 24, or the like. The individual components of the data management apparatus 20 are connected to each other by a bus 25.

The controller 21 includes a CPU, and the like.

The controller 21 reads a system program and various processing programs stored in the storage 24, and loads the programs in a work area formed in the RAM 23. The controller 21 controls the components according to the programs.

The communicator 22 includes an LAN adapter, a router, and a TA, or the like.

The communicator 22 transmits and receives data to and from an external apparatus connected to the communication network N.

The data management apparatus 20 is respectively connected by the communicator 22 to the medical image management apparatuses 12 and the medical image display apparatuses 13 in the plurality of medical facilities via the communication network N.

The RAM 23 allows the work area to be formed. The work area temporarily stores various programs read from the storage 24, input or output data, parameters and the like, in various processes executed and controlled by the controller 21.

The storage 24 includes a hard disk, and a non-volatile semiconductor memory, or the like.

The storage 24 stores the system program and various processing programs to be executed by the controller 21, and data required for execution of these programs. For example, the storage 24 stores a web server program, an application program that operates on the web server, and the like. The controller 21 communicates with a web browser installed in external equipment through the HTTP protocol according to the web server program. The controller 21 provides various web screens for the web browser of the external equipment according to the web server program. The data management apparatus 20 functions as a web server. The external equipment described above is, for example, the medical image display apparatus 13.

The storage 24 includes a patient database 241, an examination database 242, and a medical image database 243, or the like that conform to the corresponding medical facility.

The data management apparatus 20 stores the medical image received from each medical image management apparatus 12, in the corresponding medical image database 243.

The data management apparatus 20 transmits data in each database to the medical image display apparatus 13, based on communication from each medical image display apparatus 13.

The patient database 241 stores patient information on patients who are targets of examinations conducted in the plurality of medical facilities.

The patient information is information regarding a patient. The patient information includes the patient ID, patient name, birth date, age, gender, address, phone number, and the like.

The examination database 242 stores the examination information on examinations conducted in the plurality of medical facilities.

The examination information is information regarding an examination. The examination information includes the examination ID, patient name (kanji, kana, and alphabet), birth date, gender, facility ID of a medical facility, examination date, modality, imaging portion, and examination description, or the like.

The medical image database 243 stores medical images taken by the imaging apparatuses 11 in examinations conducted in the plurality of medical facilities and received from the medical image management apparatus 12. The medical image database 243 stores the patient information, examination information, series information, image information, and the like in association with each other with respect to each medical image.

The series information is information regarding a series. The series information includes a modality (such as CT, MRI, DR, CR and US), a series instance UID, an examination portion, a series number, series description, and the like. The series instance UID is a unique ID for identifying a series. The series number is a number indicating the order of series in the same examination and is sometimes utilized as a display order, or the like.

The image information is information regarding a medical image. The image information includes the image number, image generation date, imaging direction, imaging start position, image type, and file path, or the like. The image number is a number indicating the ordinal number of the image within the same series. The imaging start position is coordinates indicating a position at which an examination (scan) is started in an examination, such as of CT or MRI. The image type is information indicating whether the image is a slice image or a scout image in the examination, such as of CT or MRI. The file path is information indicating a storage location of the medical image in the medical image database 243.

The storage 24 includes a web viewer application program (hereinafter, a web application 244).

The web application 244 is an application provided for external equipment (e.g., the medical image display apparatus 13). The controller 21 executes a process in response to an operation from the medical image display apparatus 13, through the web application 244, and provides a processing result for the medical image display apparatus 13.

Specifically, the controller 21 causes the medical image display apparatus 13 to display the medical image stored in the medical image database 243, through the web application 244. That is, the web application 244 (second viewer) displays a second medical image stored in the data management apparatus 20 (second server).

The user who operates the medical image display apparatus 13 refers to the medical image, using the web application 244.

<Operation in Medical Image Display System>

Next, operation in the medical image display system 1 is described.

Figure 4:
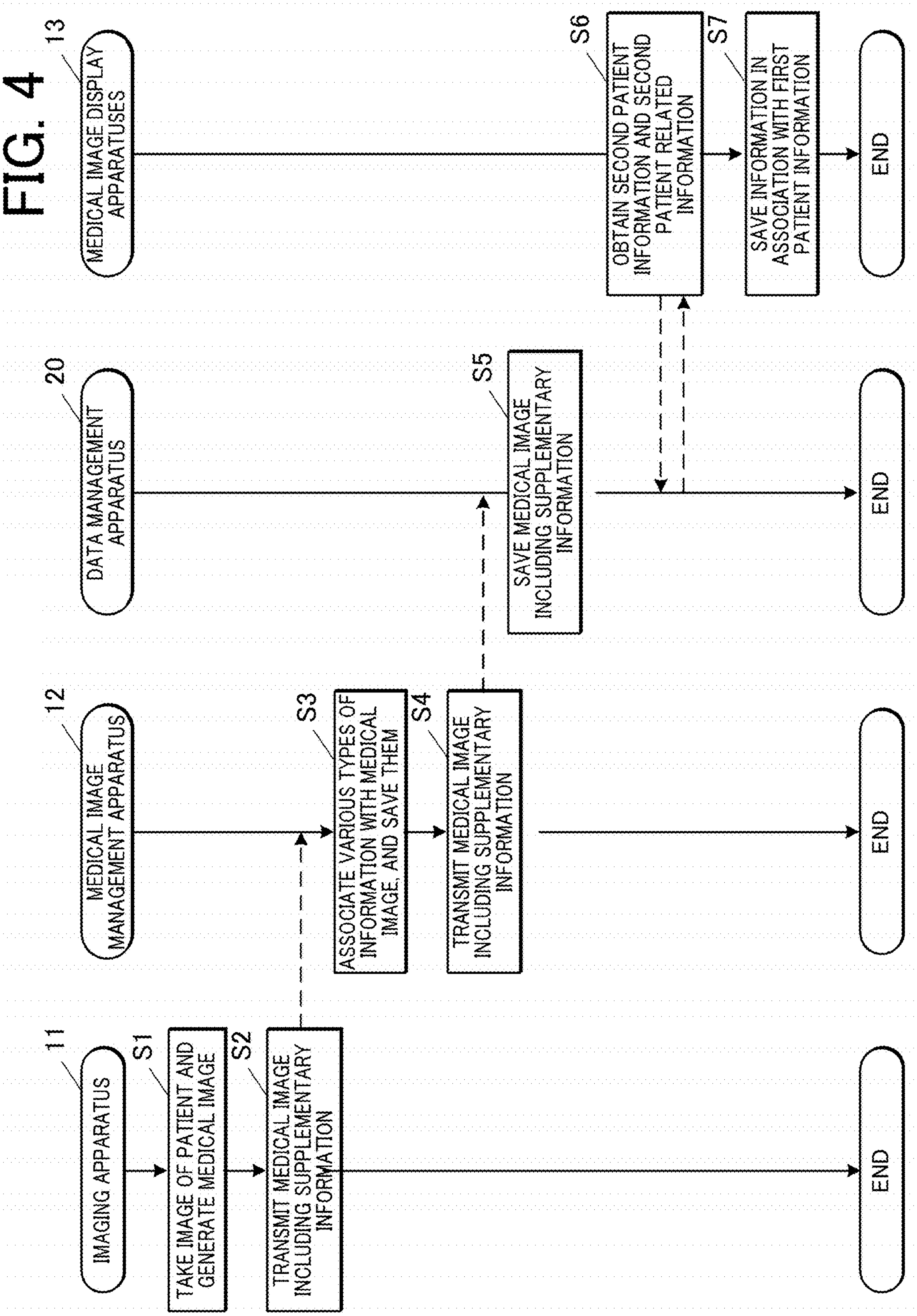
FIG. 4 is a ladder chart showing a related patient saving process.

Each apparatus of the medical image display system 1 executes a related patient saving process shown in FIG. 4.

(Related Patient Saving Process)

The imaging apparatus 11 in the medical facility takes an image of an examination target portion of a patient and generates image data of the medical image (Step S1). Hereinafter, the patient whose image is taken in Step S1 is represented as a first patient. The medical image generated in Step S1 is represented also as a first medical image.

Next, the imaging apparatus 11 transmits the medical image including supplementary information to the medical image management apparatus 12 via an intra-facility network (Step S2).

Upon receipt of the medical image including the supplementary information, the medical image management apparatus 12 associates various types of information with the medical image, and stores them in the database (Step S3). The various types of information include the patient information, examination information, image ID of the medical image, and facility ID of the medical facility, or the like.

Next, the medical image management apparatus 12 transmits a copy of the medical image stored in Step S3 to the data management apparatus 20 (Step S4).

The controller 21 of the data management apparatus 20 receives the medical image including the supplementary information, via the communicator 22. The controller 21 saves the received medical image in the medical image database 243. The controller 21 obtains the patient information from the supplementary information on the received medical image, and saves the patient information in the patient database 241. The controller 21 obtains the examination information from the supplementary information on the received medical image, and saves the examination information in the examination database 242 (Step S5).

Next, the controller 131 of the medical image display apparatus 13 obtains from the patient database 241, the patient information on a related patient similar to the patient information on the first patient (first patient information). Hereinafter, the patient information on the related patient is represented as second patient information. The controller 131 obtains from the storage 24, second patient related information that is information related to the second patient information (Step S6).

The second patient information is patient information corresponding to the medical image generated in a medical facility other than the medical facility where the first medical image has been generated.

The second patient information is patient information having absolute items coinciding with those of the first patient information and having ambiguous items with a similarity to the first patient information equal to or higher than a predetermined threshold. The predetermined threshold is preset.

The absolute items are the birth date and gender of the patient included in the patient information.

The ambiguous items are the patient name, patient address, phone number, and the like included in the patient information.

The second patient related information includes the examination information corresponding to the second patient information, a thumbnail of the medical image, and the similarity to the first patient information with respect to the ambiguous item, or the like.

Next, the controller 131 saves the second patient information and the second patient related information obtained in Step S6, in the medical image management apparatus 12 (Step S7) and finishes this processing. The controller 131 associates the second patient information with the first patient information in Step S7.

Figure 5:
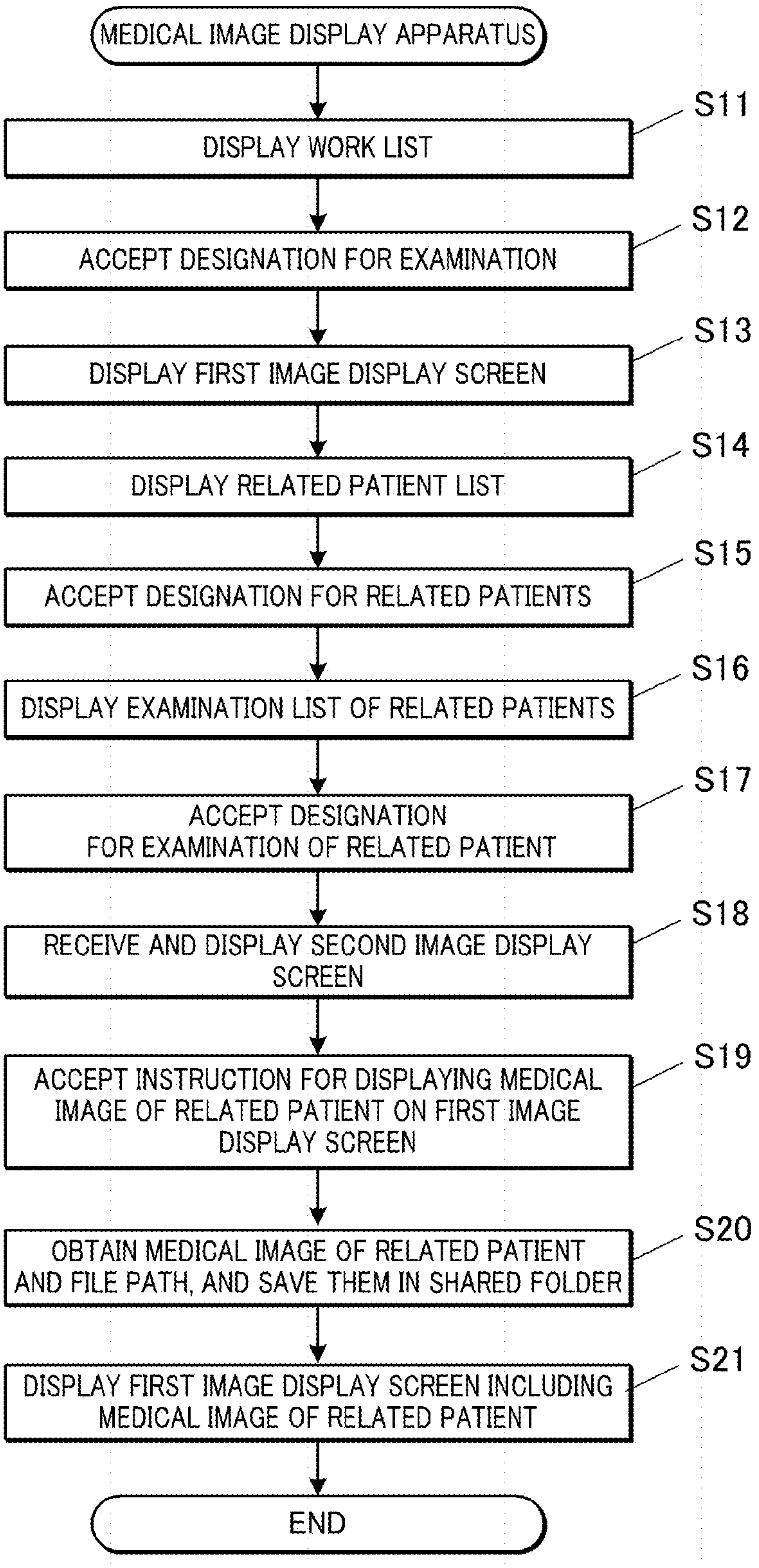
FIG. 5 is a flowchart showing a medical image display process.

Next, operation in the medical image display apparatus 13 is described. FIG. 5 is a flowchart showing a medical image display process executed by the medical image display apparatus 13.

Upon receipt of an instruction for displaying a work list WL from the user through the operation receiver 132, the controller 131 of the medical image display apparatus 13 executes the medical image display process.

(Medical Image Display Process)

The controller 131 obtains examination information on the examination conducted in the own facility from the medical image management apparatus 12. The controller 131 displays the examination list on the work list WL (see FIG. 6), based on the obtained examination information (Step S11).

Figure 6:
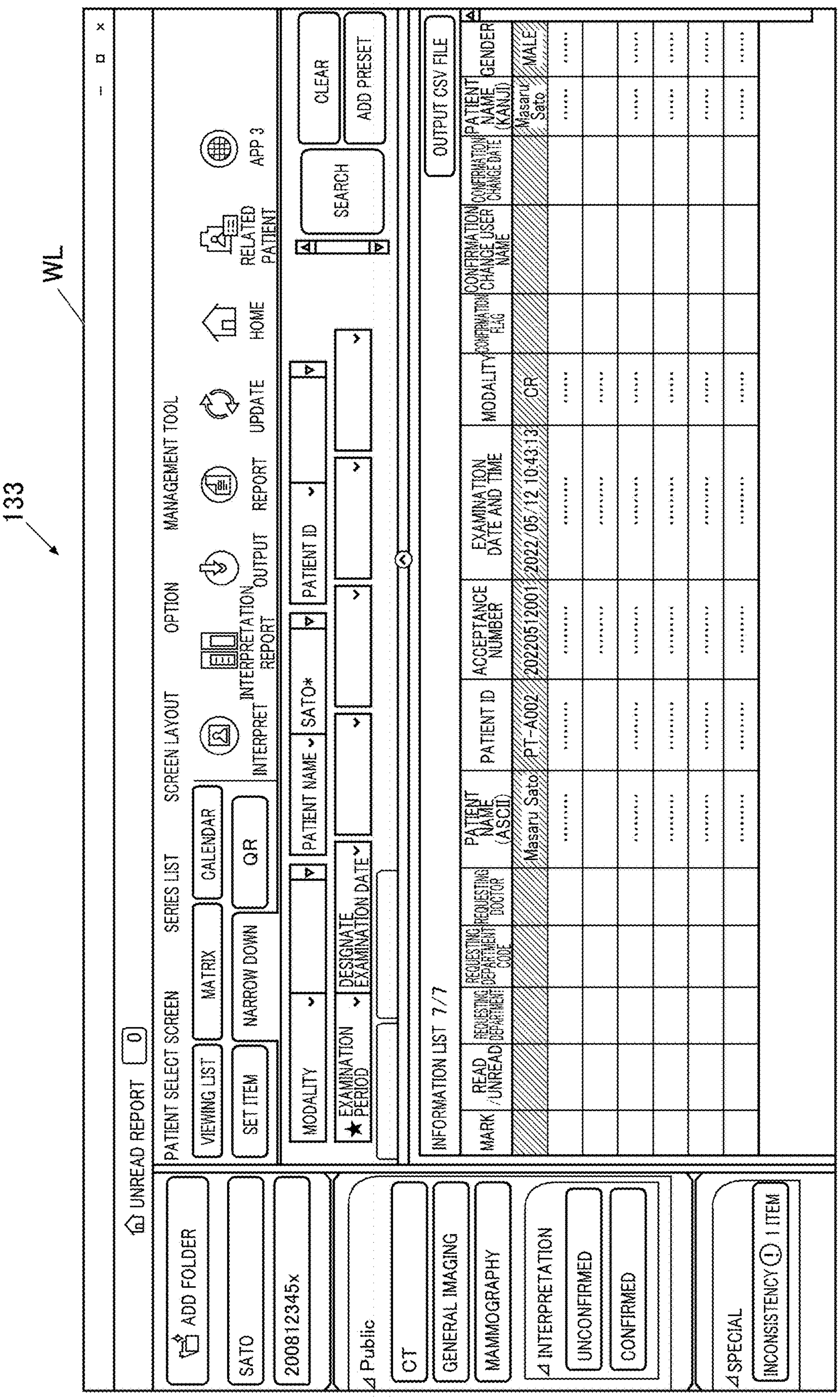
FIG. 6 shows an example of a work list where an examination list is displayed.

In FIG. 6, the controller 131 displays the examination list including a patient name of "Sato", on the work list WL.

Next, the controller 131 accepts, through the operation receiver 132, a designation by the user for the examination displayed on the work list WL (Step S12). For example, in FIG. 6, a row of "Masaru Sato" with a patient ID of PT-A002 has been clicked once and comes into a selected state accordingly. In the selected state, the same row is double-clicked, thereby designating the examination.

Next, the controller 131 obtains from the medical image management apparatus 12, the medical image taken in the examination designated in Step S12. Next, the controller 131 displays, on the display 133, a first image display screen V1 (see FIG. 7) including the obtained medical image, using the local application 136*a* (Step S13).

Figure 7:
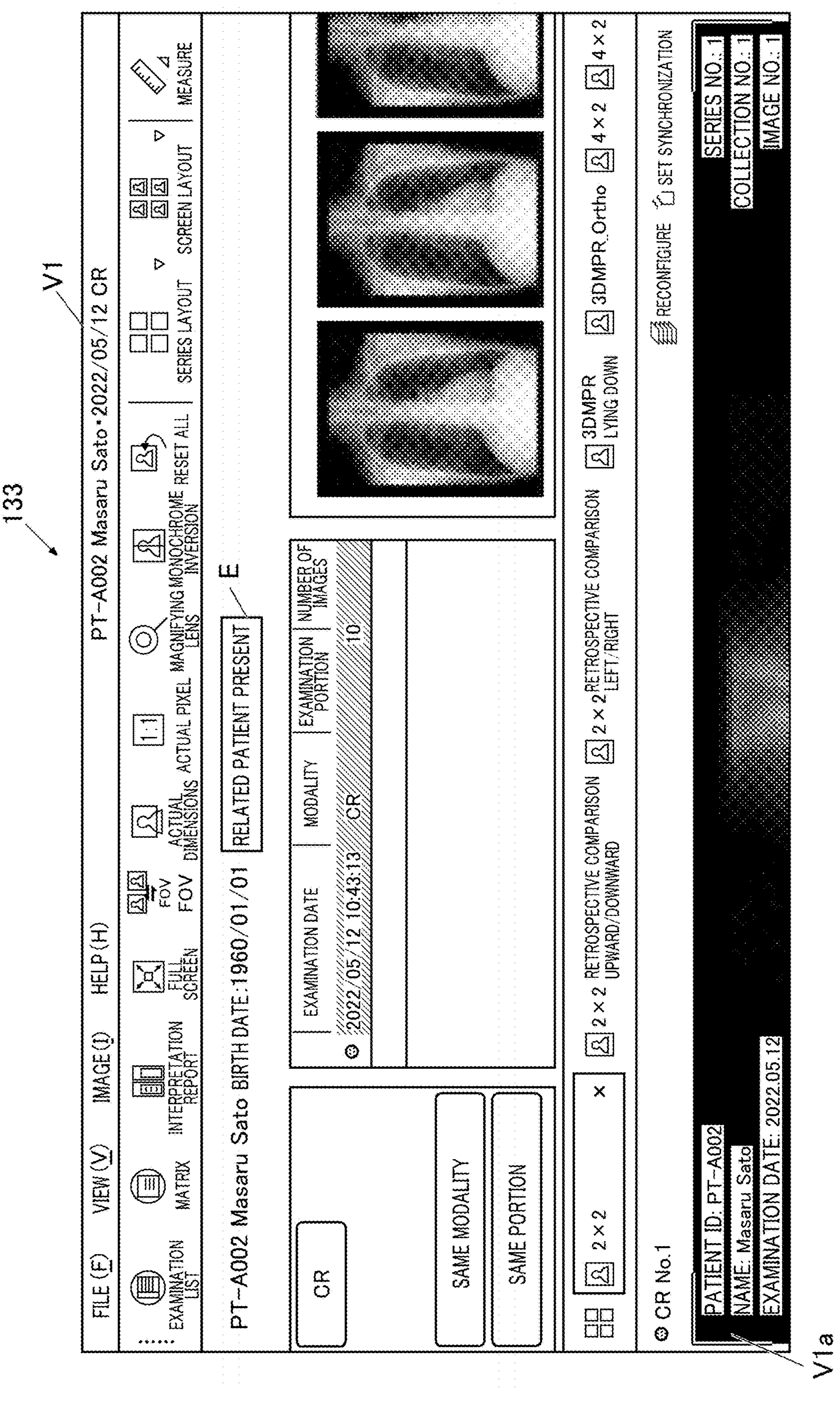
FIG. 7 shows an example of a first image display screen where medical images are displayed.

In the example shown in FIG. 7, the controller 131 displays the medical image taken in the examination designated in Step S12, in a region V1*a* on the first image display screen V1.

A case is described where the second patient information associated with the patient information in the examination designated in Step S12 is saved in the medical image management apparatus 12. In this case, the controller 131 displays presence information E on the first image display screen V1. The presence information E indicates that the second patient information associated with the patient information in the examination designated in Step S12 is present. The presence information E is, for example, a button that includes characters. However, there is no limitation to this. The presence information E may be, for example, a predetermined symbol, a mark or the like.

Next, the controller 131 accepts, through the operation receiver 132, a click operation for the presence information E by the user. Upon acceptance of the click operation for the presence information E, the controller 131 displays the related patient list (see FIG. 8) on the work list WL (Step S14). The controller 131 displays the second patient information, and the second patient related information, on the related patient list.

Figure 8:
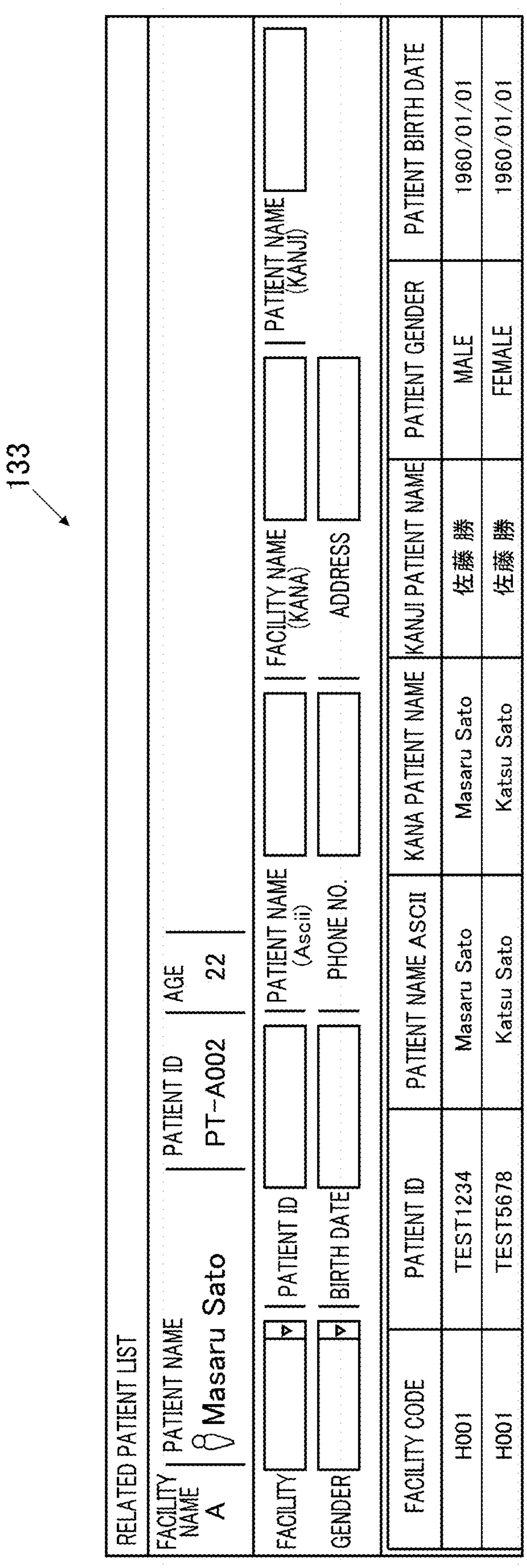
FIG. 8 shows an example of a related patient list.

In the example shown in FIG. 8, the controller 131 displays patient IDs, patient names, and birth dates of the related patients, which are the second patient information. The controller 131 displays a facility code (facility ID), which is the second patient related information.

The controller 131 may display the addresses, phone numbers and the like of the related patients, which are the second patient information, on the related patient list.

The controller 131 may display the examination information corresponding to the related patients, thumbnails of medical images, similarities to the first patient information with respect to the ambiguous item, and the like, which are the second patient related information, on the related patient list.

Next, the controller 131 accepts, through the operation receiver 132, a designation by the user about the related patient displayed on the related patient list (Step S15). The user designates a patient assumed to be identical to the patient as the target of the examination designated in Step S12, on the related patient list, for example, by double-clicking.

Next, the controller 131 obtains the examination information on the examinations to be performed on the related patients designated in Step S15, from the medical image management apparatus 12. The controller 131 displays the examination list (see FIG. 9) of the related patients designated in Step S15, on the work list WL, based on the obtained examination information (Step S16).

Next, the controller 131 accepts, through the operation receiver 132, a designation by the user for the examination displayed on the examination list of the related patient (Step S17). The user makes the designation on the examination list of the related patient by, for example, double-clicking.

Next, the controller 131 receives from the data management apparatus 20, a second image display screen V2 (see FIG. 10) for displaying the medical images taken by the examination for the related patient designated in Step S17. The controller 131 displays the received second image display screen V2 on the display 133, using the web application 244 (Step S18).

Figure 10:
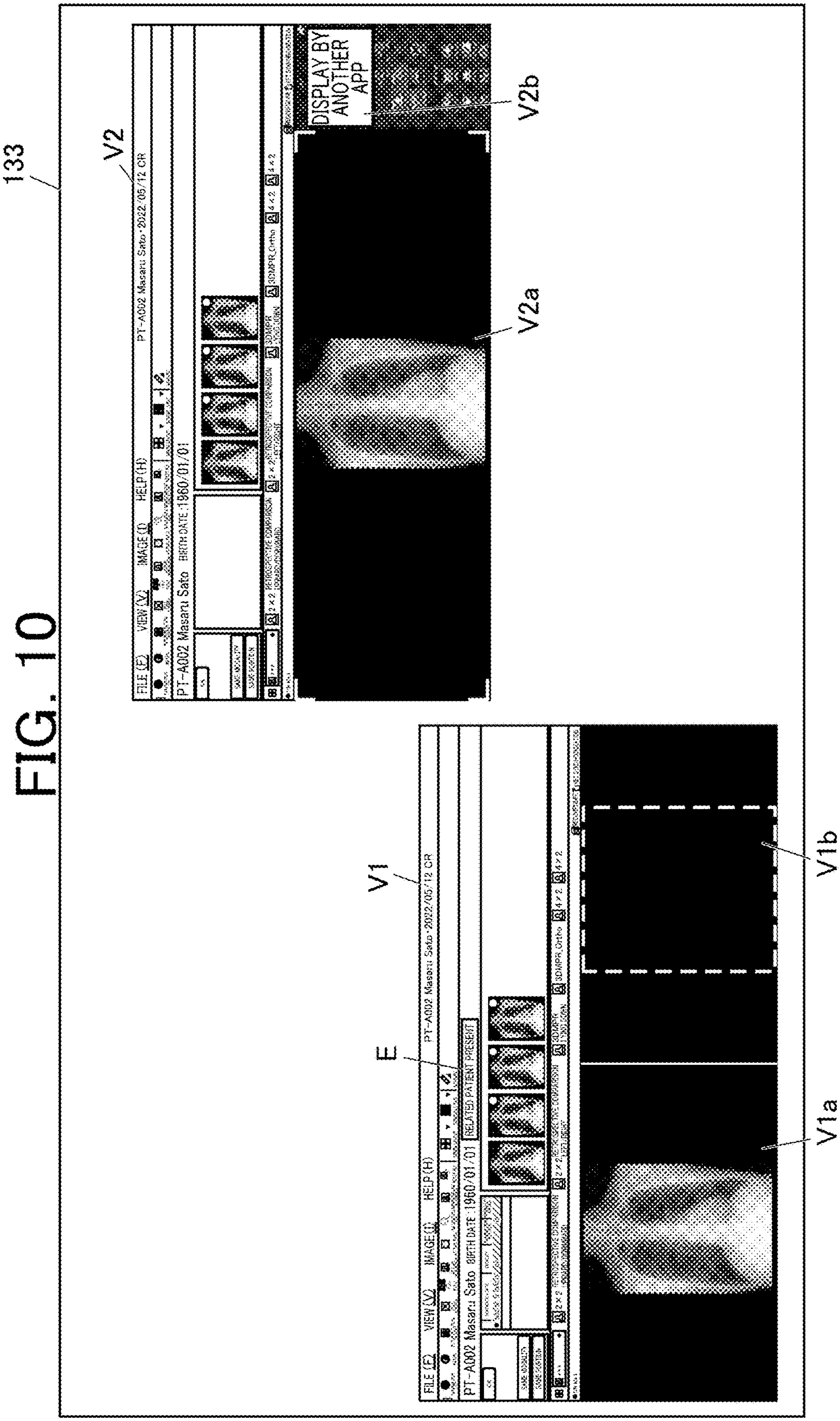
FIG. 10 shows examples of a first image display screen and a second image display screen.

In the example shown in FIG. 10, the controller 131 displays the first image display screen V1 and the second image display screen V2 on the display 133. The controller 131 displays the medical image taken in the examination designated in Step S17, in a region V2*a* in the second image display screen V2.

Next, the controller 131 accepts a predetermined operation by the user through the operation receiver 132 (Step S19). The predetermined operation is an instruction operation for displaying, on the first image display screen V1, the medical image of the related patient displayed on the second image display screen V2, using the local application 136*a*.

The instruction operation is, for example, an operation for dragging and dropping the medical image of the related patient displayed in the region V2*a* on the second image display screen V2, to a region V1*b* on the first image display screen V1.

The instruction operation may be an operation of clicking "DISPLAY BY ANOTHER APP" button V2*b* (see FIG. 10) provided on the second image display screen V2.

Next, the controller 131 receives the medical image of the related patient, and the file path to the medical image, from the medical image database 243. The medical image of the related patient is an image about which the instruction for displaying on the first image display screen V1 is accepted in Step S19. That is, the controller 131 obtains the medical image of the related patient from the data management apparatus 20 (second server). The medical image of the related patient is a related medical image that is the second medical image related to the first medical image. The controller 131 functions as an obtainer. When the related medical image is displayed by the web application 244 (second viewer), the controller 131 serving as the obtainer obtains the related medical image, based on the instruction through the operation receiver 132. Next, the controller 131 saves the received medical image of the related patient and file path to the medical image, in a shared folder (Step S20).

The shared folder may be included in the medical image management apparatus 12, in the medical image display apparatus 13, or in the data management apparatus 20.

The shared folder is a folder in which internal data can be updated and removed from both of the medical image display apparatus 13 and the data management apparatus 20.

Next, the controller 131 displays the medical image of the related patient saved in Step S20, on the first image display screen V1, using the local application 136*a* (Step S21), and finishes this processing. Specifically, the controller 131 obtains the medical image of the related patient from the shared folder. Next, the controller 131 generates the first image display screen V1 that includes the medical image of the related patient, and the medical image taken in the examination designated in Step S12 and displays the screen on the display 133. That is, the controller 131 causes the local application 136*a* (first viewer) to display the medical image of the related patient (related medical image) obtained by this controller serving as the obtainer. The controller 131 functions as a display controller.

Figure 11:
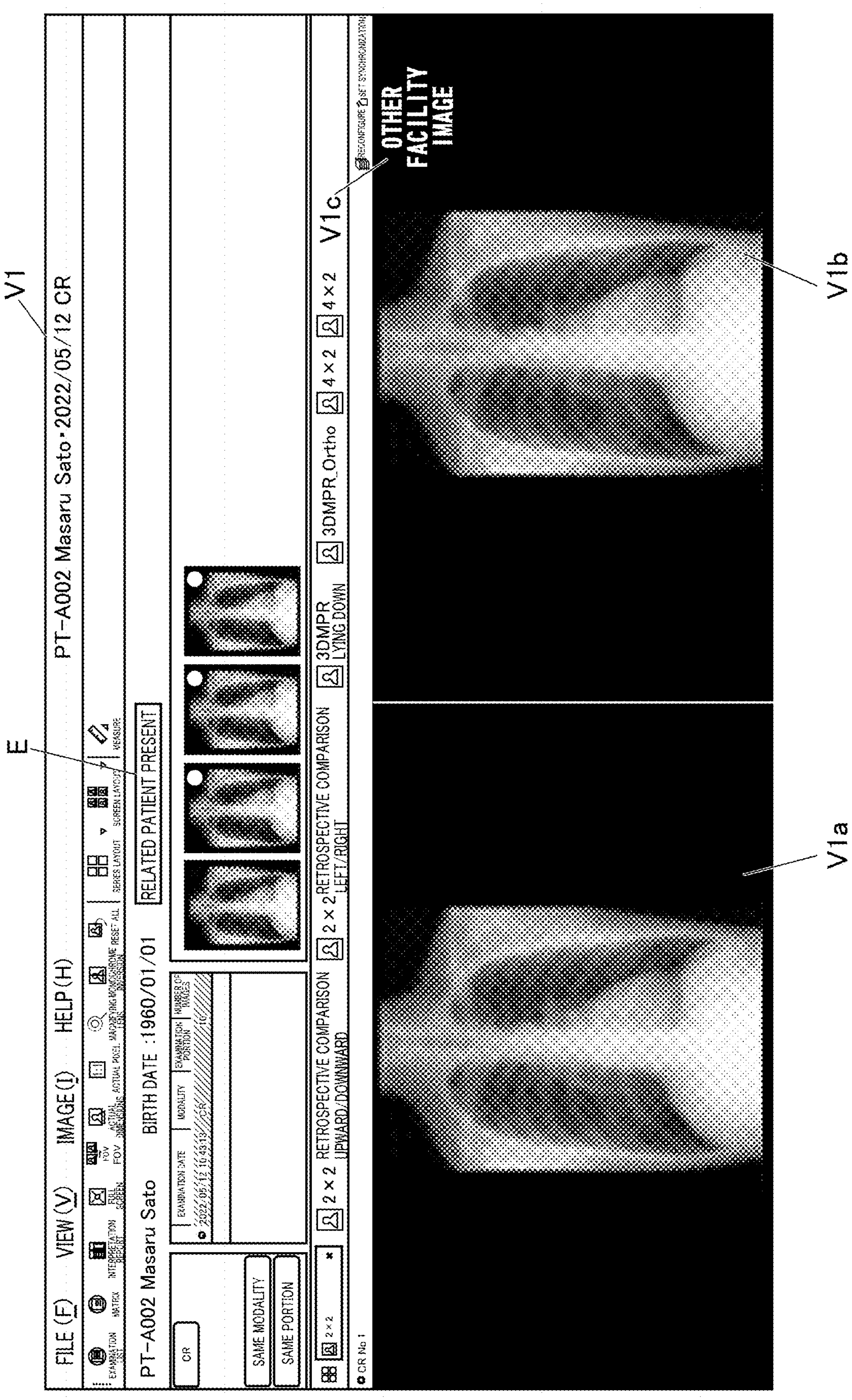
FIG. 11 shows an example of the first image display screen where medical images of the related patient are displayed.

In the example shown in FIG. 11, the controller 131 displays the medical image taken in the examination designated in Step S12, in the region V1*a* on the first image display screen V1. The controller 131 displays, in the region V1*b* on the first image display screen V1, the medical image of the related patient about which the instruction for displaying on the first image display screen V1 has been accepted in Step S19. That is, the display 133 juxtaposes and displays the first medical image, and the medical image of the related patient (related medical image), through the local application 136*a* (first viewer).

An indication V1*c* on the first image display screen V1 indicates that the medical image of the related patient displayed in the region V1*b* has been generated in a medical facility (another facility) other than the own facility.

By the medical image display process, the image taken in the own facility, and the image taken in the medical facility (other facility) other than the own facility can be juxtaposed in one application, thus allowing comparative interpretation. Accordingly, the efficiency of interpretation can be improved.

By the medical image display process, the image taken in the other facility can be displayed using the local application 136*a* in the own facility. Accordingly, the user can interpret the image taken in the other facility, by executing predetermined operations, through the local application 136*a* about which the user is experienced in operation in the own facility. The user can interpret the image taken in the other facility, using operations and functions that are distinctive to the local application 136*a*, through this local application 136*a* in the own facility.

MODIFIED EXAMPLE

Next, a modified example of the aforementioned embodiment is described.

The medical image display system in this modified example has a configuration similar to that of the medical image display system 1 described in the aforementioned embodiment. Accordingly, description and illustration of the configuration are omitted.

Figure 12:
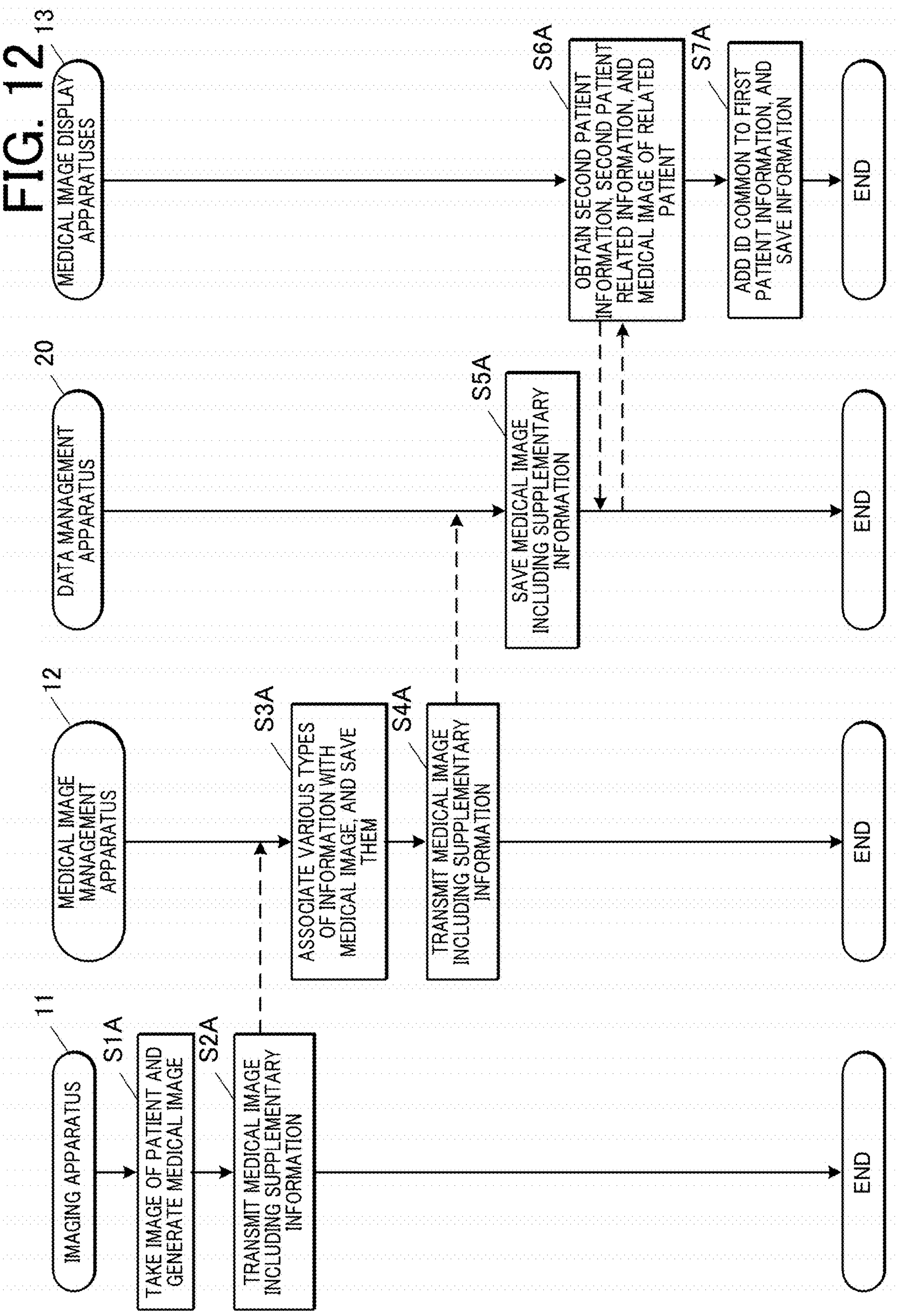
FIG. 12 is a ladder chart showing a related patient saving process in a modified example.

FIG. 12 is a ladder chart showing a related patient saving process in this modified example.

(Related Patient Saving Process in Modified Example)

The apparatuses of the medical image display system 1 execute Steps S1A to S5A similar to Steps S1 to S5 in the embodiment described above.

Next, the controller 131 of the medical image display apparatus 13 obtains the second patient information from the patient database 241. The controller 131 obtains the second patient related information from the storage 24. The controller 131 obtains from the medical image database 243, the medical image of the related patient that is the medical image corresponding to the second patient information (Step S6A). That is, the controller 131 serving as the obtainer obtains the medical image of the related patient from the data management apparatus 20 (second server). The medical image of the related patient is a related medical image that is the second medical image related to the first medical image.

Next, the controller 131 saves the second patient information, the second patient related information, and the medical image of the related patient obtained in Step S6A, in the medical image management apparatus 12 (Step S7A) and finishes this processing. That is, the controller 131 causes the medical image management apparatus 12 (first server) to store the medical image of the related patient (related medical image) obtained by this controller serving as the obtainer. The controller 131 functions as a saver.

In Step S7A, the controller 131 adds a common ID that is common identification information, to the first patient information and the second patient information. That is, the controller 131 serving as the saver adds the common identification information (common ID), to the first patient information on the patient as the subject of the first medical image, and to the second patient information on the patient as the subject of the related medical image.

The controller 131 manages the second patient information, the second patient related information, and the medical image of the related patient saved in the medical image management apparatus 12, separately from data on examinations conducted in the own facility. For example, the controller 131 do not display the second patient information and the second patient related information, on the work list for displaying the examination list conducted in the own facility.

The controller 131 removes the second patient information, the second patient related information, and the medical image of the related patient saved in the medical image management apparatus 12, after a lapse of a period shorter than a period for removal of the data on the examinations conducted in the own facility. For example, the controller 131 removes the second patient information, the second patient related information, and the medical image of the related patient, at timing when one month elapses after saving. That is, the controller 131 serving as the saver removes the medical image of the related patient stored in the first server, when a predetermined time period elapses after the medical image management apparatus 12 (first server) is caused to store the medical image of the related patient (related medical image).

The controller 131 do not add the same patient ID to the patient information on the examination conducted in the own facility, and to the second patient information.

Figure 13:
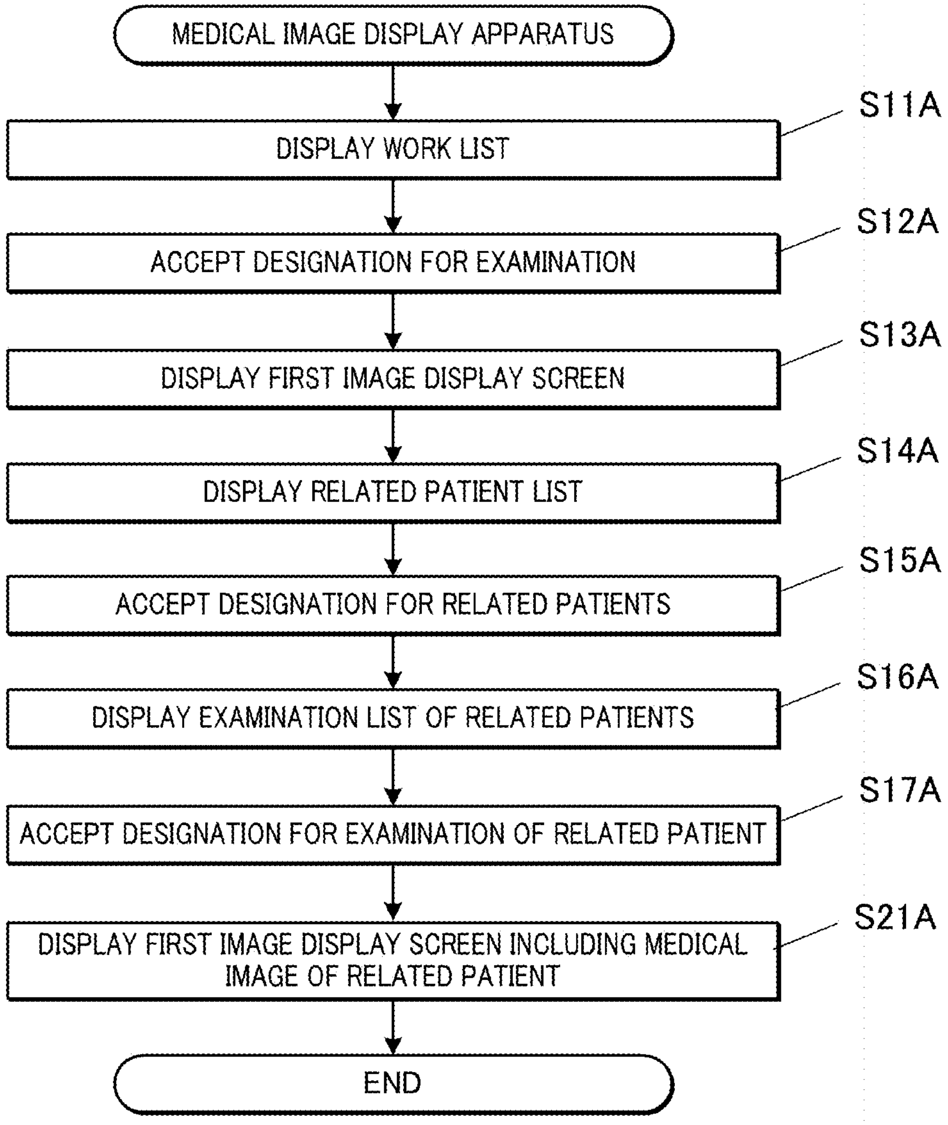
FIG. 13 is a flowchart showing a medical image display process in the modified example.

Next, the medical image display process in this modified example shown in FIG. 13 is described.

(Medical Image Display Process in Modified Example)

The controller 131 obtains examination information on the examination conducted in the own facility from the medical image management apparatus 12. The controller 131 obtains from the medical image management apparatus 12, the examination information corresponding to the second patient information saved in Step S7A. The controller 131 displays the examination list on the work list WL (see FIG. 14), based on the obtained examination information (Step S11A).

Figure 14:
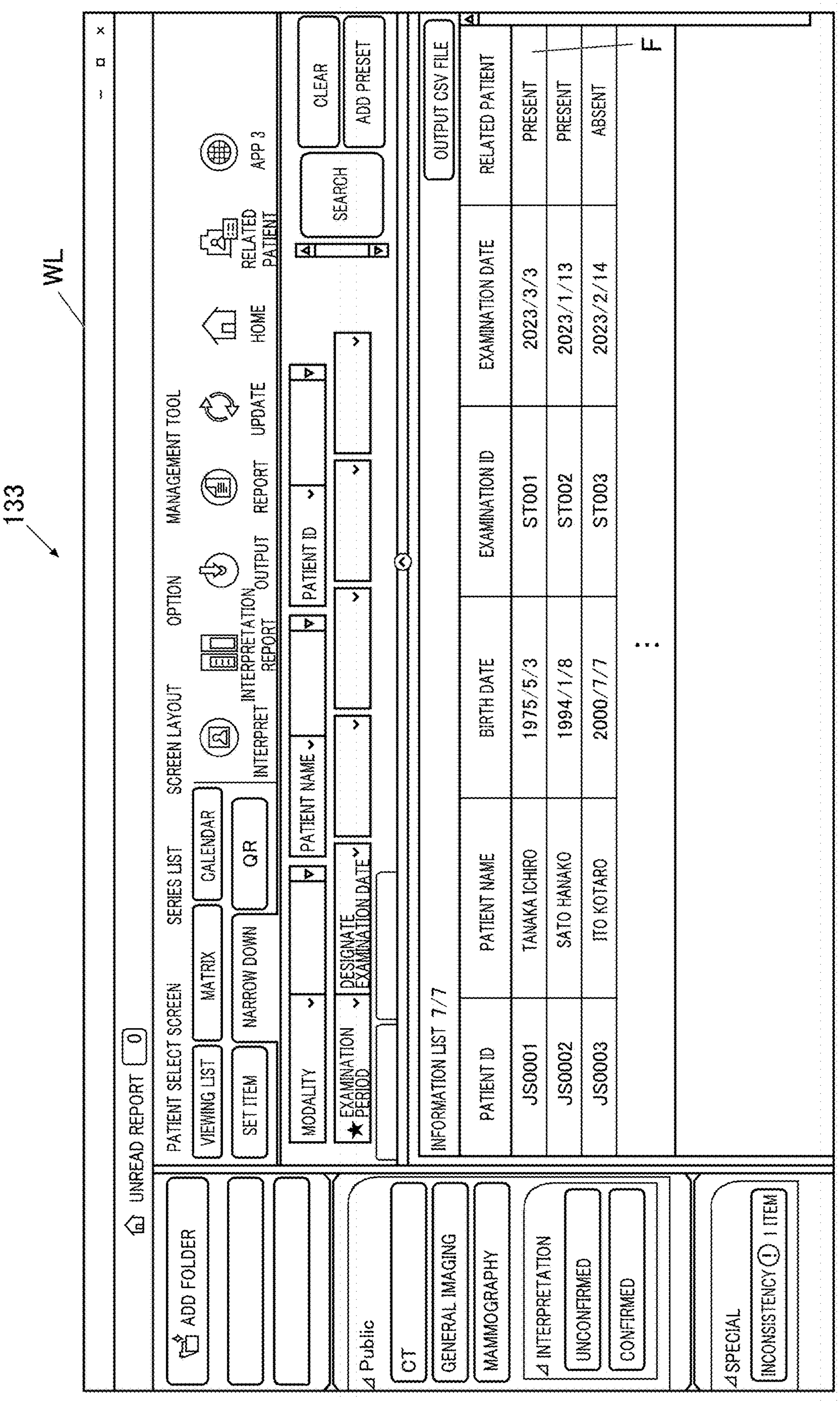
FIG. 14 shows an example of a work list where an examination list is displayed in the modified example.

In FIG. 14, the controller 131 displays the examination list in the own facility, on the work list WL. The controller 131 displays presence information F for the examination information about which the related patient is present, on the work list WL. The presence information F indicates that the second patient information associated with the patient information in the examination displayed on the work list WL is present. The presence information F is, for example, a button that includes characters. However, there is no limitation to this. The presence information F may be, for example, a predetermined symbol, a mark, or the like.

Upon acceptance of an operation of clicking the presence information F by the user through the operation receiver 132, the controller 131 displays the related patient list shown in FIG. 15, on the work list WL.

In FIG. 15, the controller 131 displays obtainment "DONE" for the related patient about whom the medical image of the related patient has been saved in the medical image management apparatus 12. The controller 131 displays information G for the related patient about whom the medical image of the related patient has not been obtained. The information G is, for example, a button that includes characters. However, there is no limitation to this. The information G may be, for example, a predetermined symbol, a mark, or the like.

Upon acceptance of an operation of clicking the information G by the user through the operation receiver 132, the controller 131 obtains the medical image of the related patient from the medical image database 243. Next, the controller 131 saves the obtained medical image of the related patient, in the medical image management apparatus 12.

Figure 16:
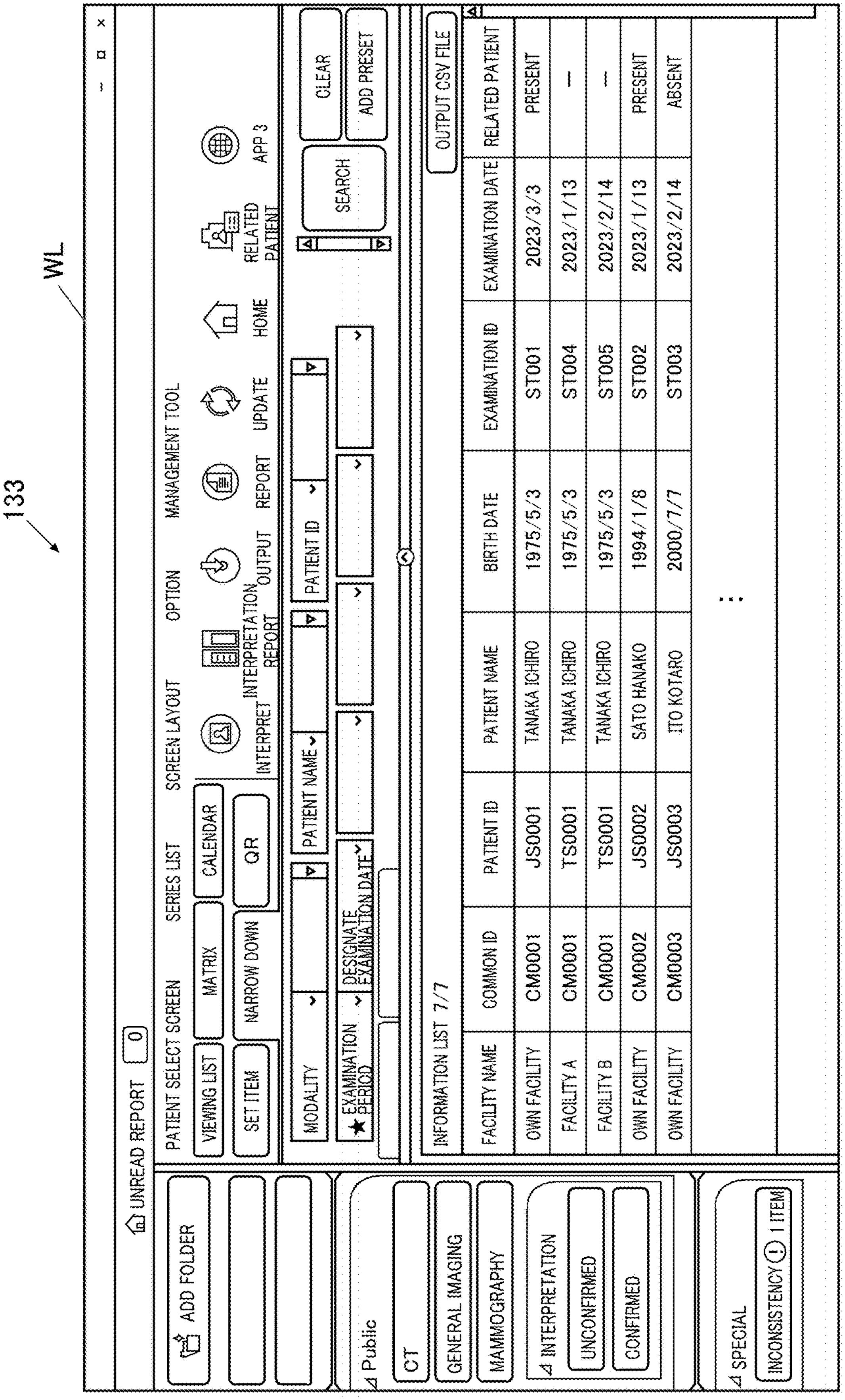
FIG. 16 shows an example of a work list where an examination list is displayed in the modified example.

FIG. 16 shows another example of the work list WL for displaying the examination list.

In FIG. 16, the controller 131 displays the list of examinations conducted in the own facility, and examinations on the related patients, on the work list WL.

The controller 131 displays the facility names in which the examinations have been conducted, on the work list WL. Accordingly, the user can discriminate the examinations in the own facility and the examinations on the related patients (examinations in other facilities) from each other.

The controller 131 displays the common ID added to the patient information on the examination in the own facility, and to the second patient information, on the work list WL.

Returning to FIG. 13, the controller 131 accepts, through the operation receiver 132, a designation by the user for the examination in the own facility displayed on the work list WL (Step S12A).

Next, the controller 131 executes Steps S13A to S17A similar to the Steps S13 to S17 in the embodiment described above.

Next, the controller 131 displays, on the display 133, the first image display screen V1 that includes the medical image taken in the examination on the related patient designated in Step S17A (Step S21A). The controller 131 finishes this processing. Specifically, the controller 131 obtains from the medical image management apparatus 12, the medical image taken in the examination on the related patient designated in Step S17A. Next, the controller 131 generates the first image display screen V1 that includes the obtained medical image of the related patient, and the medical image taken in the examination designated in Step S12A. The controller 131 displays the first image display screen V1 on the display 133, using the local application 136*a*. That is, the controller 131 serving as the display controller causes the local application 136*a* (first viewer) to display the related medical image obtained by this controller serving as the obtainer.

Next, in this modified example, another facility updating process executed by the controller 131 of the medical image display apparatus 13 is described.

A case is described where the second patient information or the examination information in the second patient related information saved in the related patient saving process step S7A described above is updated (changed) in another facility. In this case, the controller 131 invalidates the common ID added to the updated second patient information. Alternatively, the controller 131 invalidates the common ID added to the second patient information corresponding to the updated examination information. That is, if the second patient information is changed, the controller 131 serving as the saver invalidates the common ID (common identification information). FIG. 17 shows an example of the examination list in this case.

In FIG. 17, the examination on the first row of the examination list is an examination conducted in the own facility. The examination on the second row of the examination list is an examination on the related patient having not been updated. The examination on the third row of the examination list is an examination on the related patient having been updated in the other facility.

The controller 131 displays a button H and a button I on the examination on the related patient having been updated in the other facility.

Upon acceptance of an operation of clicking the button H by the user, the controller 131 revalidates the invalidated common ID. Upon acceptance of an operation of clicking the button I by the user, the controller 131 removes the common ID. The common ID is a common ID added to the second patient information updated in the other facility, and the patient information on the examination in the own facility.

Next, in this modified example, an own facility updating process executed by the controller 131 of the medical image display apparatus 13 is described.

A case is described where the patient information or the examination information in the examination in the own facility to which the common ID has been added in the related patient saving process step S7A described above is updated (changed) in the own facility. In this case, the controller 131 invalidates the common ID added to the updated patient information. Alternatively, the controller 131 invalidates the common ID added to the patient information corresponding to the updated examination information. That is, if the first patient information is changed, the controller 131 serving as the saver invalidates the common ID (common identification information). The first patient information is patient information in the examination in the own facility. FIG. 18 shows an example of the examination list in this case.

In FIG. 18, the examination on the first row of the examination list is the examination corresponding to the patient information or the examination information updated in the own facility. The examinations on the second and third rows of the examination list are examinations corresponding to the second patient information to which the common ID identical to that of the examination on the first row is added.

The controller 131 displays a button J and a button K to the examinations on the second and third rows of the examination list.

Upon acceptance of an operation of clicking the button J by the user, the controller 131 re-executes the related patient saving process steps S6A and S7A described above. That is, in Step S7A, the controller 131 adds a valid common ID to the patient information and the second patient information updated in the own facility.

Upon acceptance of an operation of clicking the button K by the user, the controller 131 removes the common ID. The common ID is a common ID added to the patient information and the second patient information updated in the own facility.

The controller 131 may validate or remove the common ID added to the updated patient information, based on the amount of change in similarity to the second patient information with respect to the ambiguous item before and after the update. In this case, the controller 131 accepts setting of a threshold for the amount of change from the user, in a common ID setting screen shown in FIG. 19.

In FIG. 19, if the amount of change in similarity is 80% or more, the controller 131 removes the common ID added to the updated patient information. If the amount of change in similarity is less than 20%, the controller 131 validates the common ID added to the updated patient information. The amount of change in similarity is equal to or more than 20% and less than 80%, the controller 131 accepts removal or validation of the common ID through an instruction operation by the user.

Advantageous Effects

As described above, the medical image display apparatus 13 in the present embodiment includes: the display 133 that displays the first medical image stored in the first server (medical image management apparatus 12) through the first viewer (local application 136*a*); and the obtainer (controller 131) that obtains the related medical image that is the second medical image related to the first medical image, from the second server (data management apparatus 20) that stores the second medical image displayable through the second viewer (web application 244). The display 133 displays the related medical image obtained by the obtainer through the first viewer.

Accordingly, the second medical image can be displayed using the local application 136*a*. Consequently, the user can interpret the second medical image, by executing a predetermined operation, through the local application 136*a* about which the user is experienced in operation. The user can interpret the second medical image, using operations and functions that are distinctive to the local application 136*a*, through the local application 136*a*. That is, the medical image can be preferably interpreted.

In the medical image display apparatus 13 in the present embodiment, the display 133 juxtaposes and displays the first medical image and the related medical image, through the first viewer (local application 136*a*).

Accordingly, the user can easily compare and interpret the first medical image and the related medical image (medical image of the related patient) through the local application 136*a*.

The medical image display apparatus 13 in the present embodiment includes the operation receiver 132 operated by the user. The display 133 displays the related medical image through the second viewer (web application 244). When the related medical image is displayed through the second viewer, the obtainer (controller 131) obtains the related medical image, based on an instruction through the operation receiver 132.

Accordingly, at timing when the user issues a predetermined instruction, the second medical image can be displayed using the local application 136*a*.

The medical image display apparatus 13 in the present embodiment includes the saver (controller 131) that causes the first server (medical image management apparatus 12) to store the related medical image (medical image of the related patient) obtained by the obtainer (controller 131). The saver removes the related medical image stored in the first server when a predetermined time period elapses after the related medical image is stored in the first server.

Thus, the medical image of the related patient can be managed as a temporarily saved image.

In the medical image display apparatus 13 in the present embodiment, the saver (controller 131) adds common identification information (common ID) to first patient information on a patient who is a subject of the first medical image, and to second patient information on a patient who is the subject of the related medical image.

Accordingly, the first patient information on the patient as the subject of the first medical image, and the second patient information can be associated with each other.

In the medical image display apparatus 13 in the present embodiment, when the first patient information or the second patient information is changed, the saver (controller 131) invalidates the common identification information (common ID).

Accordingly, the association between the first patient information and the second patient information can be invalidated.

In the medical image display apparatus 13 in the present embodiment, the first medical image is the image generated in the first facility (own facility). The second medical image is the image generated in the second facility (other facility).

Accordingly, the medical image in the other facility (second medical image) can be displayed using the local application 136*a* in the own facility. Consequently, the user can interpret the medical image in the other facility, by executing a predetermined operation, through the local application 136*a* about which the user is experienced in operation. The user can interpret the medical image in the other facility, using operations and functions that are distinctive to the local application 136*a*, through the local application 136*a* in the own facility. That is, the medical image can be preferably interpreted.

The description in the aforementioned embodiment is an example of the medical image display system according to the present invention. There is no limitation to this. Detailed configurations and detailed operation of the individual apparatuses that constitute the system can be changed as appropriate within a range not deviating from the spirit of the present invention.

For example, in the related patient saving process step S6 described above, the controller 131 obtains the second patient information similar to the first patient information from the patient database 241. However, there is no limitation to this. The controller 131 may obtain the second patient information from the medical image management apparatus 12 via, for example, a virtual private network (VPN).

In the medical image display process step S20 described above, the controller 131 obtains the medical image of the related patient, and the file path to the medical image, from the medical image database 243. However, there is no limitation to this. The controller 131 may obtain the medical image of the related patient, and the file path to the medical image, from the medical image management apparatus 12 in the other facility via, for example, VPN.

A case is described where the medical image of the related patient is, for example, a CT or MRI image, and a plurality of medical images are generated in one imaging action. In this case, in the medical image display process step S20, the controller 131 may receive all the medical images generated in one imaging action from the medical image database 243. The controller 131 may receive some of the medical images generated in one imaging action from the medical image database 243. Alternatively, the controller 131 may accept selection of whether all the medical images generated in one imaging action are received, or some of the images is received.

A computer-readable medium that stores a program for executing each kind of processing is not limited to the above-described example, and a portable recording medium can be applied. Further, as a medium that provides data of the program via a communication line, a carrier wave may be applied.

Although embodiments of the present invention have been described and illustrated in detail, the disclosed embodiments are made for purposes of illustration and example only and not limitation. The scope of the present invention should be interpreted by terms of the appended claims.

What is claimed is:

1. A medical image display apparatus, comprising:

a display that displays, through a first viewer, a first medical image stored in a first server; and an operation receiver that an operator operates; and a hardware processor that obtains a related medical image that is a second medical image related to the first medical image and is displayable through a second viewer, from a second server that stores the second medical image, wherein the display displays the related medical image through the second viewer;

wherein, when the related medical image is displayed through the second viewer, the hardware processor obtains the related medical image from the second server based on an instruction from the operation receiver, and saves the obtained related medical image, together with a file path to the related medical image, in a shared folder in which internal data is updatable and removable from both the medical image display apparatus and the second server, wherein the display displays, through the first viewer, the related medical image obtained from the shared folder by the hardware processor;

wherein the hardware processor causes the first server to store the related medical image obtained by the hardware processor, when a predetermined time period elapses after the first server is caused to store the related medical image, the hardware processor removes the related medical image stored in the first server; and wherein the related medical image is obtained only when requested by an operator.

2. The medical image display apparatus according to claim 1, wherein the display juxtaposes and displays the first medical image and the related medical image, through the first viewer.

3. The medical image display apparatus according to claim 1, wherein the hardware processor adds common identification information to first patient information on a patient who is a subject of the first medical image, and to second patient information on a patient who is a subject of the related medical image.

4. The medical image display apparatus according to claim 3, wherein when the first patient information or the second patient information is changed, the hardware processor invalidates the common identification information.

5. The medical image display apparatus according to claim 1, wherein the first medical image is a medical image generated in a first facility, and the second medical image is a medical image generated in a second facility.

6. A non-transitory computer readable recording medium storing a program causing a computer of a medical image display apparatus to:

cause a display to display, through a first viewer, a first medical image stored in a first server; and obtain a related medical image that is a second medical image related to the first medical image and is displayable through a second viewer, from a second server that stores the second medical image, wherein the display displays the related medical image through the second viewer;

wherein, when the related medical image is displayed through the second viewer, the hardware processor obtains the related medical image from the second server based on an instruction from an operation receiver operated by an operator, and saves the obtained related medical image, together with a file path to the related medical image, in a shared folder in which internal data is updatable and removable from both the medical image display apparatus and the second server, wherein the program causes the computer to display the obtained related medical image from the shared folder through the first viewer;

wherein the hardware processor causes the first server to store the related medical image obtained by the hardware processor, when a predetermined time period elapses after the first server is caused to store the related medical image, the hardware processor removes the related medical image stored in the first server; and wherein the related medical image is obtained only when requested by an operator.

7. The recording medium according to claim 6, wherein the program causes the computer to juxtapose and display the first medical image and the related medical image, through the first viewer.

8. The recording medium according to claim 6, wherein the program causes the computer to add common identification information to first patient information on a patient who is a subject of the first medical image, and to second patient information on a patient who is a subject of the related medical image.

9. The recording medium according to claim 8, wherein when the first patient information or the second patient information is changed, the program causes the computer to invalidate the common identification information.

10. The recording medium according to claim 6, wherein the first medical image is a medical image generated in a first facility, and the second medical image is a medical image generated in a second facility.

11. A medical image display system, comprising:

a first server that stores a first medical image displayable through a first viewer;

a second server that stores a second medical image displayable through a second viewer; and a medical image display apparatus that displays a medical image, wherein the medical image display apparatus comprises:

a display that displays, through the first viewer, the first medical image stored in the first server; and an operation receiver that an operator operates; and a hardware processor that obtains a related medical image that is the second medical image related to the first medical image, from the second server, and wherein the display displays the related medical image through the second viewer;

wherein, when the related medical image is displayed through the second viewer, the hardware processor obtains the related medical image from the second server based on an instruction from the operation receiver, and saves the obtained related medical image, together with a file path to the related medical image, in a shared folder in which internal data is updatable and removable from both the medical image display apparatus and the second server, the display displays, through the first viewer, the related medical image obtained from the shared folder by the hardware processor;

wherein the hardware processor causes the first server to store the related medical image obtained by the hardware processor, when a predetermined time period elapses after the first server is caused to store the related medical image, the hardware processor removes the related medical image stored in the first server; and wherein the related medical image is obtained only when requested by an operator.

* * * * *